United States Patent [19]

Sugitachi et al.

[11] 4,273,873

[45] Jun. 16, 1981

[54] PREPARATION OF ANTITHROMBOGENIC POLYMERIC MATERIALS

[75] Inventors: Akio Sugitachi, Uozaki-kitamachi; Kunihiko Takagi, Kyoto; Yasunori Yabushita, Uji, all of Japan

[73] Assignee: Unitika Ltd., Amagasaki, Japan

[21] Appl. No.: 844,856

[22] Filed: Oct. 25, 1977

[51] Int. Cl.$^3$ .......................... C12N 11/08; A61F 1/00
[52] U.S. Cl. ............................................ 435/180; 3/1; 424/33; 424/78; 424/79; 424/94; 435/181; 435/215
[58] Field of Search ................... 195/63, 68, DIG. 11; 3/1; 424/32, 94, 33, 31, 39, 55, 78, 79; 435/215, 180, 181, 174

[56] References Cited

U.S. PATENT DOCUMENTS

| | | | |
|---|---|---|---|
| 3,511,684 | 5/1970 | Huffaker | 3/1 X |
| 3,625,745 | 12/1971 | Wright et al. | 424/31 X |
| 3,634,123 | 1/1972 | Eriksson et al. | 3/1 X |
| 3,639,213 | 2/1972 | Ginger et al. | 195/68 X |
| 3,673,612 | 7/1972 | Merrill et al. | 3/1 |
| 3,865,615 | 2/1975 | Manly | 3/1 X |
| 4,055,635 | 10/1977 | Green et al. | 195/DIG. 11 X |

OTHER PUBLICATIONS

Kunihiko, T., Immobilized Fibrin–Dissolving Enzyme For Prosthetics, Chemical Abstracts, vol. 86, 5/30/77 (161349m).
Zaborsky, O., Immobilized Enzymes, CRC Press, Cleveland, Ohio, 1973 (pp. 146–147).

*Primary Examiner*—David M. Naff
*Attorney, Agent, or Firm*—Sughrue, Rothwell, Mion, Zinn and Macpeak

[57] ABSTRACT

Antithrombogenic polymeric materials are prepared by bonding a synthetic fibrinolytic compound or a combination of a synthetic fibrinolytic compound and a fibrinolytic enzyme to a polymeric material. Bonding is preferably by covalent or ionic bonding. The antithrombogenic polymeric materials are useful for preparing various types of medical articles that come into contact with blood.

11 Claims, No Drawings

PREPARATION OF ANTITHROMBOGENIC POLYMERIC MATERIALS

BACKGROUND OF THE INVENTION

1. Field of the Invention

This invention relates to a process for preparing an antithrombogenic polymeric material.

2. Description of the Prior Art

In recent years, polymeric materials have come into use in the field of biomedical materials. The use of polymeric materials at sites directly in contact with blood, for example, as vascular prostheses, catheters, artificial kidneys, artificial hearts, lungs and sutures, presents a problem of thrombus formation. Thrombus formation means the conversion of fibrinogen in the blood ultimately to fibrin through a series of complicated enzymatic reactions involving many coagulation factors. Simultaneous with the formation of fibrin in blood coagulation, the fibrin formed continuously dissolves in a fibrinolytic system with an equilibrium being maintained.

Past development and research on antithrombogenic materials are based mainly on a study of the blood coagulation system, and have been directed to the inhibition of the conversion of fibrinogen to fibrin by applying heparin, which acts as an inhibitor for the blood coagulation system, to the surface of the material. Very few prior attempts have started from the fibrinolytic system.

U.S. Pat. No. 3,625,745 discloses a process for forming a thin, continuous adherent coating on a substrate by surface photopolymerization of a synthetic fibrinolytic compound, and an antithrombogenic article. The thus-produced article exhibits some degree of antithrombogenic character, but certain problems arise. For example, it is impossible to coat the surface of an article having a complicated shape or the inside surface of a narrow tube using surface photopolymerization. Furthermore, since the strength of the bond between the polymeric film obtained by surface photopolymerization and the substrate is weak, it is difficult to maintain the antithrombogenic character for long periods of time in the blood stream.

SUMMARY OF THE INVENTION

An object of this invention is to provide a simple and effective antithrombogenic polymeric material which has overcome the above disadvantages.

The antithrombogenic material of this invention is generally produced by the process of this invention which comprises treating a polymeric material with a solution of a synthetic fibrinolytic compound thereby to cause the synthetic fibrinolytic compound to bond to or adsorb on the polymeric material.

DETAILED DESCRIPTION OF THE INVENTION

More specifically, the process for producing the antithrombogenic polymeric material of this invention includes various embodiments as described below.

(1) In a first embodiment, the process of this invention comprises treating a polymeric material having a reactive functional group capable of forming a covalent bond with a solution of a synthetic fibrinolytic compound to bond the synthetic fibrinolytic compound covalently to the polymeric material.

(2) In a second embodiment of this invention, the process of this invention comprises treating a polymeric material having an anion exchange group with a solution of a synthetic fibrinolytic compound capable of forming an anion, thereby to ionically bond the synthetic fibrinolytic compound to the polymeric material.

(3) In a third embodiment, this invention provides a process comprising treating a polymeric material with a solution of a synthetic fibrinolytic compound in a solvent capable of wetting, swelling or dissolving the polymeric material and of dissolving the synthetic fibrinolytic compound, thereby to cause the synthetic fibrinolytic compound to be adsorbed on the polymeric material.

(4) In a fourth embodiment, this invention provides a process comprising treating a polymeric material with a solution of a synthetic fibrinolytic compound and a solution of a fibrinolytic enzyme, thereby to cause the synthetic fibrinolytic compound and the fibrinolytic enzyme to bond to or adsorb on the polymeric material.

Although the fibrinolytic enzyme has a high activity, its activity gradually decreases due to the effects of inhibitor substances present in the living body. In contrast, the synthetic fibrinolytic compound used in this invention is not inhibited in vivo, and an antithrombogenic material having a long-term effect can be obtained by the present invention.

Biomedical articles can be produced from the antithrombogenic polymeric material produced in this invention in a number of ways, for example:

(1) an antithrombogenic biomedical article can be produced by subjecting a preformed biomedical article to the process of this invention or (2) an antithrombogenic polymeric material can be produced in accordance with the process of this invention and an antithrombogenic biomedical article can be then produced from the thus produced material.

The synthetic fibrinolytic compound used in this invention is less expensive than naturally obtained fibrinolytic enzymes, and since the process of this invention is simple in operation, an antithrombogenic material of low cost can be obtained.

In one embodiment of the invention in which both a synthetic fibrinolytic compound and a fibrinolytic enzyme are bonded to or adsorbed on the polymeric material, the synthetic fibrinolytic compound has the effect of increasing the activity of the fibrinolytic enzyme. Hence, the amount of the fibrinolytic enzyme, which is expensive, can be reduced, and an antithrombogenic material having a long-term effect can be obtained.

The term "synthetic fibrinolytic compound" is used in this invention to describe a synthetic compound which contributes to the dissolution of fibrin, and includes, for example, 1,2-diphenylpyrazolidine derivative, anthranilic acid derivatives, salicylic acid derivatives, cinnamic acid derivatives, $\beta$-aryl substituted aliphatic acids, and carboxylic acids containing a heterocyclic ring.

More specifically suitable synthetic fibrolytic compounds useful in this invention include the following compounds:

(1) 1,2-Diphenylpyrazolidine Derivatives having the general formulae (I) and (II)

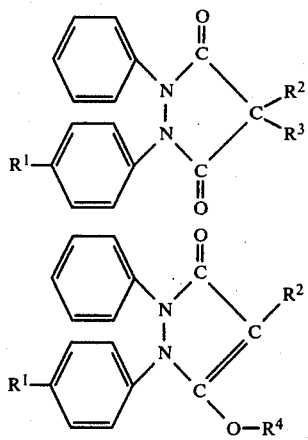

(I)

(II)

wherein

R[1] is a hydrogen atom or a hydroxyl group;

R[2] is an unsubstituted alkyl having 1 to 8 carbon atoms or an alkyl group substituted with at least one of an oxo group, a hydroxy group, a cyclohexyl group, a phenyl group, a furyl group, a carboxy group, a salicyloyl group, a 4-hydroxyphenyl group, a methoxyphenyl group and a hydroxymethyl group as a substituent;

R[3] is a hydroxymethyl group, a 2-carboxyethyl group, or a 2-carboxyethoxymethyl group; and R[4] is a benzoyl group, a 4-chlorobenzoyl group, a 4-nitrobenzoyl group or a 2-carboxyethyl group;

(2) Anthranilic Acid Derivatives having the general formula (III)

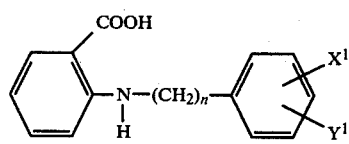

(III)

wherein n is 0 or 2 and X[1] and Y[1], which may be the same or different, each represents a hydrogen atom, a methyl group, a chlorine atom, or a trifluoromethyl group, when n is 0; and X[1] and Y[1] each is a hydrogen atom when n is 2;

(3) Salicylic Acid Derivatives having the general formula (IV)

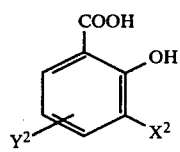

(IV)

wherein X[2] is a benzyl group, a 3-chlorobenzyl group, a 2-chlorobenzyl group, a 4-isopropylbenzyl group, a 1,1,3,3-tetramethylbutyl group, a 1,1-dimethylpropyl group, a tert-butyl group, an isopropyl group, a cinnamyl group, or an iodine atom; and Y[2] is a hydrogen atom, an iodine atom, a hydroxy group or a methyl group;

(4) Cinnamic Acid Derivatives having the general formula (V)

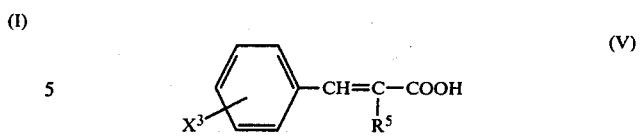

(V)

wherein X[3] is a chlorine atom, a nitro group, a bromine atom or an iodine atom; and R[5] is an alkyl group having 1 to 3 carbon atoms;

(5) β-Aryl-substituted Aliphatic Acids having the general formula (VI)

(VI)

wherein X[4] is a hydrogen atom, an alkyl group having 1 to 4 carbon atoms, a chlorine atom, a bromine atom, a methoxy group or a trifluoromethyl group; and R[6] is an alkyl group having 1 to 3 carbon atoms;

(6) Carboxylic acid containing a heterocyclic ring in which the carboxyl group is bonded directly to or through an alkylene chain to a heterocyclic ring which can be a 5- or 6-membered ring and can contain one or more of a nitrogen atom and a sulfur atom as hetero atoms, e.g.,

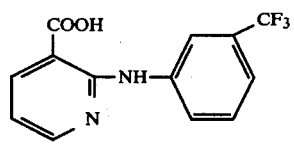

niflumic acid

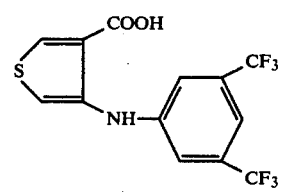

3-[3,5-di(trifluoromethyl)anilino]-
4-thiophene carboxylic acid

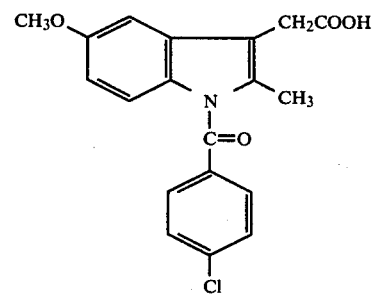

indomethacin

-continued

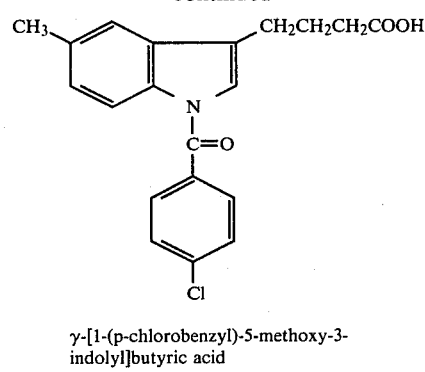

γ-[1-(p-chlorobenzyl)-5-methoxy-3-indolyl]butyric acid

Specific useful examples of these synthetic fibrinolytic compounds are listed below.

(1) 1,2-Diphenylpyrazolidine Derivatives

Phenylbutazone
Oxyphenbutazone
Ketophenylbutazone
4-(4,4-Dimethyl-3-oxopentyl)-1,2-diphenyl-3,5-pyrazolidinedione
4-(3-Oxopentyl)-1,2-diphenyl-3,5-pyrazolidinedione
4-(3-Oxo-4-methylpentyl)-1,2-diphenyl-3,5-pyrazolidinedione
4-(3-Oxo-3-cyclohexylpropyl)-1,2-diphenyl-3,5-pyrazolidinedione
4-(3-Oxo-5-methylhexyl)-1,2-diphenyl-3,5-pyrazolidinedione
4-(3-Oxo-5,5-dimethylhexyl)-1,2-diphenyl-3,5-pyrazolidinedione
4-(2-Benzoylethyl)-1,2-diphenyl-3,5-pyrazolidinedione
4-[2-(2-Furoyl)ethyl]-1,2-diphenyl-3,5-pyrazolidinedione
4-(2-Saliciloylethyl)-1,2-diphenyl-3,5-pyrazolidinedione
4-[2-(4-Hydroxybenzoyl)ethyl]-1,2-diphenyl-3,5-pyrazolidinedione
4-(3-Oxo-4-phenylpentyl)-1,2-diphenyl-3,5-pyrazolidinedione
4-(3-Oxo-4-phenyl-4-methylpentyl)-1,2-diphenyl-3,5-pyrazolidinedione
4-(3-Oxo-4-phenylhexyl)-1,2-diphenyl-3,5-pyrazolidinedione
4-(3-Oxo-1-carboxybutyl)-1,2-diphenyl-3,5-pyrazolidinedione
4-(3-Oxo-1-phenylbutyl)-1,2-diphenyl-3,5-pyrazolidinedione
4-[3-Oxo-1-(4-methoxyphenyl)butyl]-1,2-diphenyl-3,5-pyrazolidinedione
4-[3-Oxo-1-(2-furyl)butyl]-1,2-diphenyl-3,5-pyrazolidinedione
4-[2-(2-Furoyl)-1-phenylethyl]-1,2-diphenyl-3,5-pyrazolidinedione
4-[2-(2-Furoyl)-1-(4-methoxyphenyl)ethyl]-1,2-diphenyl-3,5-pyrazolidinedione
4-[2-(2-Furoyl)-1-(2-furyl)ethyl]-1,2-diphenyl-3,5-pyrazolidinedione
4-(2-Benzoyl-1-carboxyethyl)-1,2-diphenyl-3,5-pyrazolidinedione
4-[2-Benzoyl-1-(2-furyl)ethyl]-1,2-diphenyl-3,5-pyrazolidinedione
4-[4,4-Dimethyl-3-oxopentyl-1-(2-furyl)]-1,2-diphenyl-3,5-pyrazolidinedione
4-(4,4-Dimethyl-3-oxopentyl)-1-(4-hydroxyphenyl)-2-phenyl-3,5-pyrazolidinedione
4-(4,4-Dimethyl-3-hydroxypentyl)-1-(4-hydroxyphenyl)-2-phenyl-3,5-pyrazolidinedione
4-(4,4-Dimethyl-3-hydroxypentyl)-1-(4-hydroxyphenyl)-2-phenyl-3,5-pyrazolidinedione
4-(4,4-Dimethyl-3-hydroxypentyl)-1,2-diphenyl-3,5-pyrazolidinedione
4-(4-Methyl-4-hydroxy-3-oxopentyl)-1,2-diphenyl-3,5-pyrazolidinedione
4-(4,4-Dimethyl-3-oxopentyl)-5-benzoyloxy-1,2-diphenyl-3-pyrazolone
4-(4,4-Dimethyl-3-oxopentyl)-5-(4-chlorobenzoyloxy)-1,2-diphenyl-3-pyrazolone
4-(4,4-Dimethyl-3-oxopentyl)-5-(4-nitrobenzoyloxy)-1,2-diphenyl-3-pyrazolone
4-Butyl-4-hydroxymethyl-1,2-diphenyl-3,5-pyrazolidinedione
4-(3-Oxobutyl)-4-hydroxymethyl-1,2-diphenyl-3,5-pyrazolidinedione
4-(4,4-Dimethyl-3-oxopentyl)-4-hydroxymethyl-1,2-diphenyl-3,5-pyrazolidinedione
4-(2-Benzoylethyl)-4-hydroxymethyl-1,2-diphenyl-3,5-pyrazolidinedione
4-(2-Carboxyethyl)-4-butyl-1,2-diphenyl-3,5-pyrazolidinedione
4-Butyl-5-(2-carboxyethoxy)-1,2-diphenyl-3-pyrazolone
4-Butyl-4-hydroxymethyl-1,2-diphenyl-3,5-pyrazolidinedione semisuccinate (2) Anthranilic Acid Derivatives N-Phenylanthranilic acid
N-(3-Methylphenyl)anthranilic acid
N-(2-Methylphenyl)anthranilic acid
N-(3,5-Dimethylphenyl)anthranilic acid
Mefenamic acid
Flufenamic acid
N-(2-trifluoromethylphenyl)anthranilic acid
N-[3,5-di(Trifluoromethyl)phenyl]anthranilic acid
N-(2-Phenylethyl)anthranilic acid
N-(3-Trifluoromethyl-4-chlorophenyl)anthranilic acid (3) Salicyclic Acid Derivatives 3-(3-Chlorobenzyl)salicyclic acid
3-(2-Chlorobenzyl)salicyclic acid
3-(4-Isopropylbenzyl)salicylic acid
3-(1,1,3,3-Tetramethylbutyl)salicylic acid
3,5-Diiodosalicylic acid
3-(1,1-Dimethylpropyl)salicylic acid
3-tert-Butylsalicylic acid
3-Benzyl-γ-resorcylic acid
3-Cinnamylsalicylic acid
o-Thymotic acid (4) Cinnamic Acid Derivatives α-Methyl-p-chlorocinnamic acid
α-Ethyl-p-chlorocinnamic acid
α-Ethyl-m-chlorocinnamic acid
α-Propylcinnamic acid
α-Propyl-m-nitrocinnamic acid
α-Propyl-m-chlorocinnamic acid
α-Propyl-p-chlorocinnamic acid
α-Propyl-m-bromocinnamic acid
α-Propyl-p-bromocinnamic acid α-Propyl-m-iodocinnamic acid
α-Propyl-p-iodocinnamic acid

(5) β-Aryl Substituted Aliphatic Acids

β-Phenyl-n-butyric acid
β-(p-Tolyl)-n-butyric acid
β-(p-Ethylphenyl)-n-butyric acid
β-(p-Isopropylphenyl)-n-butyric acid
β-(p-Isobutylphenyl)-n-butyric acid
β-(p-Chlorophenyl)-n-butyric acid
β-(p-Bromophenyl)-n-butyric acid
β-(m-Bromophenyl)-n-butyric acid
β-[m-(Trifluoromethyl)phenyl]-n-butyric acid
β-(p-Methoxyphenyl)-n-butyric acid
β-Phenyl-n-valeric acid
β-(p-Tolyl)-n-valeric acid
β-(p-Isobutylphenyl)-n-valeric acid
β-(p-Chlorophenyl)-n-valeric acid
β-Phenyl-n-caproic acid
β-(p-Tolyl)-n-caproic acid
β-(p-Chlorophenyl)-n-caproic acid
β-Phenylisocaproic acid
β-(p-Tolyl)isocaproic acid
β-(p-Isobutylphenyl)isocaproic acid

(6) Heterocyclic Ring Containing Carboxylic Acids

Niflumic acid
3-[3,5-Di(trifluoromethyl)anilino]-4-thiophene carboxylic acid
Indomethacin
γ-[1-(p-Chlorobenzyl)-5-methoxy-3-indolyl]butyric acid

(7) Other Compounds

N,N'-bis-(3-Picolyl)-4-methoxyisophthalamide
N-Lauryl-imino-di-β-propionic acid
bis-(2-Hydroxy-1-naphthyl)methane-3,3'-dicarboxylic acid The term "reactive functitonal group capable of forming a covalent bond" as used in the description of the process of this invention is employed to describe, for example, carboxy, amino, chloroformyl, diazonium, azido, epoxy, formyl, bromoacetyl, isocyanato, carboxylic acid anhydride, and imidocarbonato groups. These reactive functional groups may be present at the terminals of and/or on the side chains of and/or on the main chains of the polymeric materials.

Examples of polymeric materials having a reactive functional group capable of forming a covalent bond are described below.

Polyacrylic acid
Polymethacrylic acid
Polymaleic acid
Poly(maleic acid mono ester)
Polyaspartic acid
Polyglutamic acid
Alginic acid
Pectinic acid
Polyethyleneimine
Polyvinylamine
Polylysine
Polyacryloyl chloride
Polymethacryloyl chloride
Polymers of bisphenol A and epichlorohydrin
Polyacrolein
Polymaleic anhydride
Polymethacrylic anhydride Linear copolymers, crosslinked copolymers, graft copolymers, and block copolymers containing the monomers as constituents of the above-exemplified polymers can also be used in and are included within the scope of this invention. A suitable molecular weight for these polymeric materials will depend on the mechanical strength desired for the biomedical article, but generally is more than about 7,000, preferably more than 10,000.

The above-exemplified polymeric materials have reactive functional groups capable of forming a covalent bond with the synthetic fibrinolytic compound in amounts sufficient to render the polymeric material antithrombogenic, i.e., to increase the time at which thrombus formation occurs to greater than about 30 minutes. Sufficient amounts of reactive functional groups can be introduced by a polymer reaction into polymeric materials which contain little or no functional groups capable of forming a covalent bond. Polymeric materials having sufficient amounts of reactive functional groups can also be subjected to a reaction in order to convert the functional groups to other reactive functional groups.

Examples of polymeric materials into which reactive functional groups capable of forming a covalent bond can be introduced, and methods for their introduction are described below. The methods used to introduce these functional groups may be selected from known methods.

(1) Introduction of a carboxyl group

Polymeric materials containing a hydroxyl group, such as cellulose, cellulose acetate, polyvinyl alcohol, starch, etc., can be carboxymethylated, e.g., as disclosed in U.S. Pat. No. 2,523,377, to obtain polymers with a carboxyl group as a reactive functional group.

(2) Introduction of an amino group

Polymeric materials containing a terminal carboxyl group, such as polyamides (e.g., nylon-6, nylon-6,6, nylon-11, nylon-12) and polyesters (e.g., polyethylene terephthalate or polyester elastomers), can be reacted, e.g., as disclosed in Japanese Patent Application (OPI) 10378/77, with polyamines such as polyethyleneimine in the presence of a dehydrocondensing agent such as dicyclohexylcarbodiimide to produce polymers with an amino group as a reactive functional group.

Amination can also be performed by reacting a silicone with γ-aminopropyltriethoxysilane, e.g., as disclosed in H. H. Weetall, Science, 166, 615 (1969), to obtain polymers with an amino group as a reactive functional group.

Polypropylene, polyethylene, polyvinyl chloride, poly(methyl methacrylate), polycarbonate, polytetrafluoroethylene, polyurethane, and polyacrylonitrile may be aminated at the surface employing a gas plasma treatment using ammonia or a mixture of nitrogen and hydrogen, e.g., as disclosed in J. R. Hollahan, B. B. Stafford, R. D. Falb, and S. T. Payne, *J. Polymer Sci.*, 13, 807 (1969), to obtain polymers with an amino group as a reactive functional group.

(3) Introduction of a chloroformyl group

A carboxyl-containing polymeric material such as polymethacrylic acid or polyacrylic acid can be chlorinated with thionyl chloride, acetyl chloride, etc., e.g., as disclosed in T. Shimizu and R. L. Letsinger, *J. Org.*

*Chem.*, 708 (1968), to obtain polymers with a chloroformyl group as a reactive functional group.

(4) Introduction of a diazonium group

A polymeric material containing an aromatic amino group such as polyaminostyrene can be diazotized, e.g., as disclosed in W. E. Hornby, H. Filippusson and A. McDonald, *FEBS Letters*, 9, 8 (1970), to produce polymers with a diazonium group as a reactive functional group.

(5) Introduction of an azido group

A polymeric material containing a carboxyl group or a carboxylic ester group, such as polyacrylic acid, polymethacrylic acid, carboxymethyl cellulose, or poly(methyl methacrylate), can be converted to an azido derivative through a hydrazino derivative, e.g., as disclosed in M. A. Mitz and L. J. Summaria, *Nature*, 189, 576 (1961), to produce polymers containing an azido group as a reactive functional group.

(6) Introduction of an epoxy group

Polybutadiene can be epoxidized and phenol-novolac resins can be glycidylated, e.g., as disclosed in T. Otsu, M. Kondo, S. Aoki and M. Imoto, J. Appl. Polymer Sci, 9, 1991 (1965), to obtain polymers with an epoxy group as a reactive functional group.

(7) Introduction of a formyl group

Starch can be oxidized (the formation of dialdehyde starch), e.g., as disclosed in E. L. Jackson and C. S. Hudson, *J. Am. Chem. Soc.*, 59, 2049 (1937), to obtain polymers with a formyl group as a reactive functional group.

(8) Introduction of a bromoacetyl group

A hydroxyl-containing polymeric material, such as polyvinyl alcohol or cellulose, can be bromoacetylated by reaction with bromoacetyl bromide, e.g., as disclosed in Israeli Pat. No. 18207 (1965), to obtain polymers with a bromoacetyl group as a reactive functional group.

(9) Introduction of an isocyanato group

An amino-containing polymeric material, such as polyaminostyrene or an aniline-formaldehyde resin, can be reacted with phosgene to produce polymers with an isocyanato group as a reactive functional group, e.g., as disclosed in H. Brandenfurger, Angeco. Chem., 67, 661 (1955).

(10) Introduction of an imidocarbonato group

A hydroxyl-containing polymeric material, such as cellulose, agarose or dextran, can be reacted with cyanogen bromide to form an imidocarbonate derivative, e.g., as disclosed in R. Axen, J. Porath and S. Ernback, Nature, 214, 1302 (1967), as a polymer containing an imidocarbonato group as a reactive functional group.

(11) Introduction of a carboxylic acid anhydride group

Polymaleic acid or poly(maleic acid mono ester) can be cyclized by heat-dehydration, e.g., by heating at higher than about 100° C. for longer than about 5 hours under a reduced pressure of less than about 10 mm Hg to produce a polymer containing a carboxylic acid anhydride group as a reactive functional group.

A synthetic fibrinolytic compound can be covalently bonded to a polymeric material containing a reactive functional group capable of forming a covalent bond (or a polymeric material having a reactive functional group capable of forming a covalent bond introduced thereinto) by treating the polymeric material with a solution of the synthetic fibrinolytic compound. The reactive functional group capable of forming a covalent bond reacts with the carboxyl group, the amino group, the phenolic group, or the active hydrogen atom at the 4-position of 1,2-diphenyl-3,5-pyrazolidinedione of the synthetic fibrinolytic compound. The amount of the synthetic fibrinolytic compound used in this invention is in general an excess amount, particularly since in treating the surface of an already formed and shaped article, it is impossible to determine the amount of reactive functional groups on the surface.

The solvent used to dissolve the synthetic fibrinolytic compound should be inert to the reactive functional groups of the polymeric materials and the synthetic fibrinolytic compound. In general, a suitable concentration of the polymeric material in the solvent is about 0.01 to about 30 percent by weight, preferably 0.1 to 10 percent by weight. Examples of suitable solvents which can be used are water, methyl alcohol, ethyl alcohol, acetone, dioxane, tetrahydrofuran, benzene, toluene, chloroform, dimethylformamide, dimethylacetamide, dimethyl sulfoxide, and mixtures of these solvents. When it is desired to treat the surface of a shaped article of the polymeric material having a reactive functional group capable of forming a covalent bond, such as tubes, filaments, fabrics, films, sheets, membranes, permeable membranes or beads, a solvent which will not dissolve the polymeric material must be selected. Water or an aqueous alcohol solution can be used for materials having poor resistance to organic solvents, such as polyvinyl chloride. For materials having good organic solvent resistance such as silicones and polyamides, water, methyl alcohol, ethyl alcohol, acetone, dioxane, tetrahydrofuran, benzene, toluene, chloroform, dimethylformamide, dimethylacetamide, etc., and mixtures thereof can be used.

The treatment of the surface of the shaped polymeric article with a solution of the synthetic fibrinolytic compound is performed at a temperature of higher than the melting point of the solvent and lower than the boiling point of the solvent, and preferably about 0 to about 70° C. in the optional presence of a catalyst, e.g., in an amount of the catalyst per reactive functional group capable of forming a covalent bond of about 0.0001 to about 1 mole %, preferably 0.001 to 0.1 mol %, such as an acid, (e.g., hydrochloric acid, sulfuric acid, etc.) or an alkali (e.g., sodium hydroxide, potassium hydroxide, etc.) and a condensing agent such as dicyclohexylcarbodiimide or pyridine. Desirably, a fresh surface of the polymeric material is provided by stirring, circulation, etc. during the surface treatment.

The synthetic fibrinolytic compound can also be covalently bonded to the polymeric material having a reactive functional group capable of forming a covalent bond (or bonded to the polymeric material having a reactive functional group capable of forming a covalent bond introduced thereinto) by treating a solution of the polymeric material with a solution of the synthetic fibrinolytic compound. A suitable amount of the synthetic fibrinolytic compound per reactive functional group of the polymeric material is about 20 to about 200 mole %, preferably 40 to 100 mole %. The solvents for dissolving the polymeric material and the synthetic fibrinolytic compound should be inert to the reactive functional groups of the polymeric material and the synthetic fibrinolytic compound. Such solvents can be selected from those solvents which are used to treat the surface of the shaped articles of the polymeric material. Desirably, these solvents are miscible with each other.

The treatment of the solution of the polymeric material with the solution of the synthetic fibrinolytic compound is carried out by mixing the two solutions at a temperature of higher than the melting point of the solvent and lower than the boiling point of the solvent, and preferably about 0° to about 70° C., in the optional presence of a catalyst, e.g., in an amount of the catalyst per reactive functional group capable of forming a covalent bond of about 0.0001 to about 1 mole %, preferably 0.001 to 0.1 mole %, such as an acid (e.g., hydrochloric acid, sulfuric acid, etc.) or an alkali (e.g., sodium hydroxide, potassium hydroxide, etc.) and a condensing reagent such as dicyclohexylcarbodiimide or pyridine, e.g., in an amount of the condensing agent of about 20 to about 200 mole % per reactive functional group. In this manner, the polymeric material to which the synthetic fibrinolytic compound has been bonded covalently can be coated on the surface of a material which is to be rendered antithrombogenic. The antithromobogenic polymeric material can be isolated by evaporating off the solvent from the solution containing it or by precipitation.

spacer appropriately separates the polymeric material and the synthetic fibrinolytic compound and prevents a loss or decrease in fibrinolytic activity due to steric hindrance, and where it is impossible to covalently bond the synthetic fibrinolytic compound with the polymeric material by directly reacting the synthetic fibrinolytic compound with the polymeric material, one functional group of the spacer is reacted with the polymeric material and the other functional group of the spacer is bonded with the synthetic fibrinolytic compound. A spacer can be inserted or employed as follows: by reacting the synthetic fibrinolytic compound with one functional group of one end of the spacer and reacting the polymeric material with the other functional group of the other end of the spacer, or by reacting the polymeric material with one functional group of one end of the spacer and reacting the synthetic fibrinolytic compound with the other functional group of the other end of the spacer. Use of a spacer in bonding a ligand to an insoluble support is well known in the field of affinity chromatography, for example, as disclosed in *Methods in Enzymology*, Vol. 34, edited by W. B. Jakoby and M. Wilchek, Academic Press, 1974, and similar approaches can be used herein in bonding the polymeric material with the synthetic fibrinolytic compound using a spacer. The use of a spacer is more specifically described by reference to the following table.

TABLE

| | | Reactive Site Present in Synthetic Fibrinolytic Compound | | | |
|---|---|---|---|---|---|
| Reactive Functional Group Present in Polymeric Material | | | | | Active Hydrogen Atom at 4-Position of |
| Method of Introduction | Reactive Functional Group | Carboxyl Group | Amino Group | Phenolic Group | 1,2-Diphenylpyrazolidinedione compound |
| (1) | Carboxyl | Spacer | — | Spacer | Spacer |
| (2) | Amino | — | Spacer | Spacer | Spacer |
| (3) | Chloroformyl | — | — | — | — |
| (4) | Diazonium | Spacer | — | — | — |
| (5) | Azido | Spacer | — | Spacer | Spacer |
| (6) | Epoxy | — | — | — | — |
| (7) | Formyl | Spacer | — | Spacer | Spacer |
| (8) | Bromoacetyl | Spacer | — | — | — |
| (9) | Isocyanato | — | — | — | Spacer |
| (10) | Imidocarbonato | Spacer | — | Spacer | Spacer |
| (11) | Carboxylic acid anhydride | Spacer | — | — | Spacer |

Note:
Where the symbol "—" is used in the above table, a covalent bond can be directly formed without the need for a spacer and where the term "spacer" is used in the above table, a covalent bond can be formed by inserting a spacer between the polymeric material and the synthetic fibrinolytic compound.

In covalently bonding the synthetic fibrinolytic compound to the polymeric material using a reactive functional group capable of forming a covalent bond, it is necessary for the synthetic fibrinolytic compound to be bonded at sites other than at the sites of a reactive group which is directly involved in fibrinolytic activity. Because of the complexity of fibrinolytic activity, often it is necessary to determine experimentally whether fibrinolytic activity is retained but such can be accomplished by routine testing to determine whether such fibrinolytic activity is retained.

If desired a spacer may be inserted between the polymeric material and the synthetic fibrinolytic compound during the formation of the covalent bond so as to prevent a loss or decrease in fibrinolytic activity due to steric hindrance.

A spacer is a chemical agent having two reactive functional groups and acts in the following manner. The In a second embodiment of the process of this invention a polymeric material having an anion exchange group is used. The term "anion exchange group" is used herein to describe, for example, a primary amino group, a secondary amino group, a tertiary amino group, a quaternary ammonium group, a sulfonium group or a quaternary phosphonium group, and the anion exchange group can be present at the terminals of, and/or on the side chains of, and/or on the main chains of the polymeric material. In the anion exchange, the anion of the anion exchange group is exchanged for that of the synthetic fibrinolytic compound and the latter is thereby adsorbed on the polymeric material.

Examples of polymeric materials containing such an anion exchange group include the following materials.
Poly(vinylamine)

Reaction products of diamines and epichlorohydrin
Condensation products of diamines and formaldehyde
Poly(dialkylaminoethyl methacrylate)
Poly(dialkylaminomethyl styrene)
Poly(vinylpyridine)
Polyethyleneimine
Poly(2-methacryloxyethyl trialkyl ammonium ion)
Poly(vinylbenzyl trialkyl ammonium ion)
Poly(N,N-dialkyl-3,5-methylenepiperidinium ion)
Poly(vinyl N-alkylpyridinium ion)
Poly(dialkyloctamethylene ammonium ion)
Poly(2-acryloxyethyl dialkyl sulfonium ion)
Poly(vinylbenzyl dialkyl sulfonium ion)
Poly(vinylbenzyl trialkyl phosphonium ion)
Poly(2-acryloxyethyl trialkyl phosphonium ion)
Poly(dialkylethylene phosphonium ion).

The counter ion for the ammonium, sulfonium or phosphonium ion is an anion, for example, such as chloride, bromide, iodide, sulfate, nitrate, carboxylate, or hydroxide.

Copolymers, grafted copolymers and block copolymers containing the monomers forming the above-exemplified homopolymers as constituents are also included within the definition of the polymeric material containing an anion exchange group, hereinafter sometimes described as an anion exchange resin.

The above polymeric materials comprising an anion exchange resin contain anion exchange groups, which can be ionically bonded to the synthetic fibrinolytic compound capable of forming an anion, in an amount sufficient to render the polymeric material antithrombogenic, i.e., in an amount sufficient to increase the thrombus formation time to greater than about 30 minutes. An anion exchange group in a sufficient amount can be introduced by a polymer reaction into polymeric materials which have little or no anion exchange groups. Anion exchange groups which can be introduced by a polymer reaction are, for example, primary amino, secondary amino, and tertiary amino groups.

Examples of polymeric materials into which anion exchange groups can be introduced and methods of introduction of these groups are described below. The method of introduction can be selected from heretofore known methods.

(1) Polyamides, such as nylon-6, nylon-6,6, nylon-11 or nylon-12, or polyesters, such as poly(ethylene terephthalate) or polyester elastomers, can be reacted with polyamines such as polyethyleneimine, e.g., as described in Japanese Patent Application (OPI) 10378/77, to introduce primary, secondary or tertiary amino groups into the polymers. The amino groups can be quaternized with an alkyl halide such as ethyl bromide or methyl iodide. The quaternization can be conducted, e.g., by reaction at 0°–50° C. for one hour to one week using an aqueous solution of an alkyl halide, such as ethyl bromide and methyl iodide, or in an alcohol solution containing water. If the reaction solvent is water, the quaternization reaction can be quickly completed but the quaternization reaction time increases as the amount of alcohol increases when a mixture of an alcohol and water is used.

(2) An amino group may be introduced into polypropylene, polyethylene, polyvinyl chloride, poly(methyl methacrylate), polycarbonate, polytetrafluoroethylene, polyurethane, polyacrylonitrile, etc. employing a gas plasma treatment using ammonia or a mixture of nitrogen and hydrogen e.g., as described in J. R. Hollahan, B. B. Stafford, R. D. Falb, and S. T. Payne, *J. Polymer Sci.*, 13, 807 (1969). The amino groups can be quaternized with an alkyl halide as described above.

(3) A tertiary amino group can be introduced by reacting polysaccharides such as cellulose, cellulose acetate, dextran, or starch with N,N-dimethylaminoethyl chloride, e.g., as disclosed in E. A. Peterson and H. A. Sober, *J. Am. Chem. Soc.*, 78, 751 (1956). The amino group can be quaternized using an alkyl halide as described above.

(4) Polyvinyl alcohol can be acetalized with aminoacetaldehyde dimethyl acetal to introduce a primary amino group into the polymer, e.g., as disclosed in U.S. Pat. No. 2,739,059.

Further, in order to produce polymeric materials into which anion exchange groups have been introduced, a sulfonium group can be introduced by reacting poly(-chloromethylstyrene) and a dialkyl sulfide, e.g., as disclosed in U.S. Pat. No. 3,078,259, and a quaternary phosphonium group can be introduced by reacting poly(chloromethylstyrene) and a trialkyl phosphine, e.g., as disclosed in U.S. Pat. No. 3,168,502.

A suitable molecular weight for the polymeric material having an anion exchange group therein is that necessary to achieve the mechanical strength as a biomedical articles and such generally is greater than about 7,000, preferably greater than 10,000.

The synthetic fibrinolytic compound capable of forming an anion can be ionically bonded to the polymeric material having an anion exchange group (or the polymeric material having an anion exchange group introduced thereinto) by treating the polymeric material with a solution of the synthetic fibrinolytic compound. Examples of the synthetic fibrinolytic compounds capable of forming an anion are 1,2-diphenyl-3,5-pyrazolidinedione derivatives containing one hydrogen atom at the 4-position thereof, carboxyl group containing 1,2-diphenylpyrazolidine derivatives, anthranilic acid derivatives, salicyclic acid derivatives, cinnamic acid derivatives, β-aryl substituted aliphatic acids and carboxylic acids containing a heterocyclic ring, all of which have been exemplified hereinabove.

Preferably, a polar solvents are used to dissolve the synthetic fibrinolytic compounds capable of forming an anion. A suitable concentration of the synthetic fibrinolytic compound in the solution is about 0.01 to 30% by weight, preferably 0.1 to 10% by weight. Examples of suitable polar solvents are alcohols such as methyl alcohol, ethyl alcohol, propyl alcohol, butyl alcohol, ethylene glycol monomethyl ether, diethylene glycol, and diethylene glycol monomethyl ether, ethers such as dioxane, tetrahydrofuran and diethylene glycol dimethyl ether, ketones such as acetone and methyl ethyl ketone, amides such as dimethylformamide, N-methylpyrrolidone, hexamethylphosphoramide and dimethylacetamide, water, and mixtures of these solvents.

In dissolving the synthetic fibrinolytic compound capable of forming an anion in such a solvent, an inorganic base such as sodium hydroxide, potassium hydroxide, sodium carbonate, potassium carbonate, sodium bicarbonate, or potassium bicarbonate, or an organic base such as triethylamine, pyridine, aniline, tetramethylammonium hydroxide or trimethylbenzylammonium hydroxide, e.g., in an amount of about 20 to 100 mole %, preferably 30 to 90 mole %, based on the weight of the synthetic fibrinolytic compound, may be added as needed.

When a solution of the synthetic fibrinolytic compound capable of forming an anion is contacted with the surface of a shaped article of the polymeric material containing an anion exchange group, an ionic bond is formed between the synthetic fibrinolytic compound and the polymeric material. In treating the surface of a preformed shaped article, since it is impossible to determine the amount of anionic exchange groups on the surface thereof, the amount of the synthetic fibrinolytic compound employed is an excess amount. The ionic reaction is carried out at a temperature of higher than the melting point of the solvent and lower than the boiling point of the solvent, and preferably about 0° to about 70° C. using a solvent which does not dissolve the polymeric material. If desired, a fresh surface of the shaped article is provided during the reaction.

An ionic bond may be formed between the polymeric material having an anion exchange group (or the polymeric material having an anion exchange group introduced thereinto) and the synthetic fibrinolytic compound capable of forming an anion by treating a solution of the polymeric material with a solution of the fibrinolytic compound. Where a solution of the polymeric material is treated, a suitable concentration for the solution of the polymeric material is about 0.1 to 10% by weight, preferably 0.5 to 5% by weight. Suitable solvents for both can be selected from those solvents described above used to treat the surface of polymeric shaped articles. A suitable amount of the synthetic fibrinolytic compound per anionic exchange group present in the polymeric material ranges from about 20 to about 200 mole %, preferably 40 to 100 mole %.

The treatment of the solution of the polymeric material with the solution of the synthetic fibrinolytic compound can be performed by mixing the two solutions at a temperature of higher than the melting point of the solvent and lower than the boiling point of the solvent, and preferably about 0° to about 70° C. Subsequently, the polymeric material having the synthetic fibrinolytic compound ionically bonded thereto can be coated on the surface of a material which is to be rendered antithrombogenic. A suitable coating amount ranges from about 0.01 to 100μ, preferably 0.1 to 10μ. The antithrombogenic product can be isolated by distilling off the solvent from the solution containing the antithrombogenic polymeric material and by precipitation.

Examples of polymeric materials which can be employed in the third embodiment of the process of this invention include polymers of olefins such as ethylene, propylene, 1-butene, 1-pentene and isobutylene, polymers of halogenated olefins such as vinyl chloride, vinylidene chloride, trifluoroethylene and tetrafluoroethylene, polymers of aromatic vinyl compounds such as styrene, divinyl benzene, α-methylstyrene or vinylpyridine, polymers of dienes such as butadiene or isoprene, polymers of N-vinyl compounds such as N-vinylamine or N-vinylpyrrolidone, polyvinyl alcohol and the esters thereof such as polyvinyl alcohol acetate, polymers of vinyl ethers such as vinyl methyl ether and tetramethylene glycol divinyl ether, polymers of sulfur-containing vinyl compounds such as vinyl sulfone or vinyl sulfoxide, polymers of unsaturated aldehydes such as acrolein, polymers of unsaturated ketones such as methyl vinyl ketone, polymers of α,β-unsaturated carboxylic acids such as acrylic acid, methacrylic acid, maleic acid or fumaric acid, polymers of α,β-unsaturated carboxylic acid esters such as methyl acrylate, ethyl acrylate, methyl methacrylate, ethyl methacrylate or maleic acid monomethyl ester, polymers of α,β-unsaturated carboxylic acid chlorides such as acryloyl chloride or methacryloyl chloride, polymers of α,β-unsaturated acid anhydride such as acrylic anhydride, methacrylic anhydride and maleic anhydride, polymers of α,β-unsaturated nitriles such as acrylonitrile or methacrylonitrile, polymers of α,β-unsaturated carboxylic acid amides such as acrylamide or methacrylamide, polyalkyleneimines such as polyethyleneimine, polyethers such as polyphenylene oxide, polymethylene oxide, polyethylene oxide or polytetramethylene oxide, polypeptides such as polyglutamic acid, polyalanine, polylysine, polyaspartic acid or polyphenylalanine, polyamides such as nylon-3, nylon-4, nylon-5, nylon-6, nylon-7, nylon-11, nylon-12, nylon-6,6, nylon-6,10, poly(m-phenyleneisophthalamide), or poly(p-phenylene terephthalamide), polyesters derived from polycarboxylic acids such as terephthalic acid, isophthalic acid, adipic acid, maleic acid, fumaric acid, or trimellitic acid and polyols such as ethylene glycol, propylene glycol, butylene glycol, pentaerythritol or bisphenol A, polyesters derived from hydroxycarboxylic acids such as glycolic acid, lactic acid or hydroxypivalic acid, silicone rubbers such as dimethylpolysiloxane, methylphenylpolysiloxane, methylvinylpolysiloxane, cyanoalkylmethylpolysiloxanes, and fluoroalkylmethylpolysiloxanes, polyurethanes derived from polyisocyanates such as toluene diisocyanate, xylene diisocyanate, phenylene diisocyanate, ethylene diisocyanate, diphenylmethane diisocyanate and toluene triisocyanate and polyols such as polyethylene glycol, polypropylene glycol or polyesters containing a hydroxy group at both terminals, formaldehyde resins such as phenol-formaldehyde resins, xylene-formaldehyde resins, urea-formaldehyde resins or melamine-formaldehyde resins, polymers containing a tetracyclic ring such as polyimides, polybenzimidazoles and polythiazoles, polycarbonates derived from bisphenol A and phosgene, polysulfones derived from bisphenol A and 4,4'-dichlorodiphenylsulfone, natural organic polymers such as cellulose, starch, proteins, and natural rubber, natural inorganic polymers such as glass, asbestos, clay and mica, and synthetic inorganic polymers such as polyphosphazene. A suitable molecular weight range for these polymers is greater than about 7,000, preferably greater than 10,000, for the reasons as described hereinbefore.

The synthetic fibrinolytic compound can be adsorbed on the polymeric material by dissolving the synthetic fibrinolytic compound in a solvent which wets, swells or dissolves the polymeric material and dissolves the synthetic fibrinolytically active compounds, and treating the polymeric material with this solution. A suitable concentration of the synthetic fibrinolytic compound is about 0.01 to about 30% by weight and preferably 0.1 to 10% by weight. Examples of suitable solvents which can be used are hydrocarbons such as benzene, toluene, xylene, cymene, naphthalene, tetrahydronaphthalene or cyclohexane, alcohols such as methyl alcohol, ethyl alcohol, propyl alcohol, butyl alcohol, amyl alcohol, octyl alcohol, cyclohexanol, ethylene glycol, glycerol, ethylene glycol monomethyl ether, ethylene glycol monoethyl ether, diethylene glycol, diethylene glycol monomethyl ether or diethylene glycol monoethyl ether, phenols such as phenol or cresol, ethers such as diethyl ether, diamyl ether, anisole, phenetole, benzyl ethyl ether, cresyl methyl ether, dioxane, tetrahydrofuran, ethylene glycol dimethyl ether, ethylene glycol diethyl ether, diethylene glycol dimethyl ether or diethylene glycol diethyl ether, ketones such as acetone, methyl ethyl ketone, cyclohexanone or acetophenone, acids such as formic acid or acetic acid, esters such as ethyl acetate, ethyl propionate, propyl acetate, butyl formate or butyl acetate, chlorinated hydrocarbons such as chloroform, methylene chloride, carbon tetrachloride, ethylene dichloride, tetrachloroethane, trichloroethylene or tetrachloroethylene, nitro compounds such as nitromethane or nitrobenzene, nitriles such as acetonitrile or benzonitrile, amides such as dimethylformamide, diethylformamide, dimethylacetamide, N-methylpyrrolidone or hexamethylphosphoramide, ureas such as tetramethyl urea, amines such as pyridine, aniline or quinoline, and water.

A solvent which wets, swells or dissolves the polymeric material and dissolves the synthetic fibrinolytic compound is selected from these solvents described above. If desired, two or more solvents can be used as a mixture thereof. The wettability, swellability or solubility of the polymeric material and/or the solubility of the synthetic fibrinolytic compound can be adjusted by adding thereto acids (e.g., hydrochloric acid, sulfuric acid, etc.), alkalies (e.g., sodium hydroxide, potassium hydroxide, sodium carbonate, potassium carbonate, sodium bicarbonate, potassium bicarbonate, etc.), salts (e.g., calcium chloride, sodium bromide, potassium bromide, sodium iodide, potassium iodide, tetramethylammonium bromide, etc.), etc., e.g., in an amount of about 0.1 to 30% by weight, preferably 1 to 10% by weight, based on the solution of the polymeric material or the solution of synthetic fibrinolytic compound.

Adsorption of the synthetic fibrinolytic compound on the polymeric material can be performed by contacting a solution of the synthetic fibrinolytic compound with the surface of a shaped article of the polymeric material, with the amount of the synthetic fibrinolytic compound used being an excess amount to that needed.

A solvent which does not dissolve the polymeric material should be selected, and the adsorption is effected at a temperature of higher than the melting point of the solvent and lower than the boiling point of the solvent, and preferably about 0° to about 70° C., while providing a fresh surface as desired. The synthetic fibrinolytic compound can also be adsorbed on the polymeric material by treating a solution of the polymeric material with a solution of the synthetic fibrinolytic compound. A suitable concentration of the polymeric material in the solution can range from about 0.1 to about 10% by weight, preferably 0.5 to 5% by weight. A suitable weight ratio of the synthetic fibrinolytic compound to the polymeric material is about 1:1 to about 1:50 and preferably 1:5 to 1:20. This treatment is performed by mixing the two solutions at a temperature of higher than the melting point of the solvent and lower than the boiling point of the solvent, and preferably about 0° to about 70° C., for about 10 minutes to about 10 hours, preferably 30 minutes to 5 hours. Subsequently, the solution of the polymeric material having the synthetic fibrinolytic compound adsorbed thereon can be coated on the surface of a material which is to be rendered antithrombogenic, e.g., where the thrombus formation time is greater than about 30 minutes. The antithrombogenic product can be isolated by distilling off the solvent from the solution of the antithrombogenic polymeric material and by precipitation.

The term "fibrinolytic enzyme" as used in the description of this invention denotes an enzyme which contributes to the dissolving of fibrin. Examples of fibrinolytic enzymes include, for example, plasmin, brinolase, urokinase and streptokinase. The fibrinolytic enzyme is bonded to or adsorbed on the polymeric material together with the synthetic fibrinolytic compound, e.g., in an amount necessary to increase the thrombus formation time to greater than 30 minutes. A simple method for achieving this is to treat the polymeric material with a solution of the synthetic fibrinolytic compound in the presence of the fibrinolytic enzyme. A suitable concentration for the solution of the enzyme which can be used ranges from about 10 to 100,000 units/ml, preferably 100 to 10,000 units/ml. This treatment results in the simultaneous bonding or adsorption of the fibrinolytic enzyme and the synthetic fibrinolytic compound. The fibrinolytic enzyme and the synthetic fibrinolytic compound may be stepwise bonded or adsorbed. For example, the fibrinolytic enzyme can be first bonded to or adsorbed on and then the synthetic fibrinolytic compound is bonded to or adsorbed on, or in a reverse sequence. In order to achieve this, the polymeric material is treated stepwise with separate solutions containing the fibrinolytic enzyme and the synthetic fibrinolytic compound dissolved therein. When it is desired to dissolve the fibrinolytic enzyme, a solvent which will not deactivate the enzyme must be selected. Water is preferred as a solvent which dissolves the enzyme or both the enzyme and the synthetic fibrinolytic compound. If desired, a mixture of water and water-miscible solvent such as ethyl alcohol, propyl alcohol, dioxane, tetrahydrofuran, dimethylformamide or dimethyl sulfoxide can be used.

The ion strength, pH, etc. of the enzyme solution are adjusted as needed. In the case of bonding or adsorbing the fibrinolytic enzyme together with the synthetic fibrinolytic compound, they can be covalently bonded to the polymeric material having a reactive functional group capable of forming a covalent bond in the same way as in the case of bonding or adsorbing only the synthetic fibrinolytic compound. Since the enzyme has a carboxyl group capable of forming an anion, the fibrinolytic enzyme and the synthetic fibrinolytic compound can be ionically bonded to the polymeric material containing an anion exchange group. When a solvent which wets, swells or dissolves the polymeric material and dissolves the synthetic fibrinolytic compound and the fibrinolytic enzyme, both can be adsorbed on the polymeric material.

The antithrombogenic materials obtained by the process of this invention are useful as biomedical materials which are to be used in contact with blood.

The following Examples are given to illustrate the present invention more specifically. Unless otherwise indicated herein, all parts, percents, ratios and the like are by weight.

The fibrinolytic activity was measured using a fibrin plate having a thickness of about 2 mm which was prepared by adding to an aqueous solution of human fibrinogen (0.5 g/ml) 0.2 ml, per 10 ml of the aqueous solution of human fibrinogen, of a physiological saline solution of thrombin from human plasma (25 units/ml). Specifically, a sample was placed on the fibrin plate, and allowed to stand at 37° C. for 24 hours, and then the fibrinolytic activity was evaluated by the degree of the dissolution of the fibrin membrane around the sample.

The antithrombogenic characteristic was evaluated by measuring the thrombus formation time using the Chandler rotary tube method (A. B. Chandler, *Laboratory Investigations,* 7, 110 (1958)).

EXAMPLE 1

Phenylbutazone (6.5 g) and 0.84 g of sodium hydroxide were dissolved in 60 ml of isopropanol, and then 3.2 g of β-bromopropionic acid was added to the solution. The mixture was refluxed for 3 hours. The resulting sodium bromide was separated by filtration, and the isopropanol was distilled off. The residue was dissolved in chloroform, and the chloroform solution was washed with a 0.5 N hydrochloric acid aqueous solution. The chloroform solution was purified by chromatography on silica gel to obtain 2-carboxyethyl derivatives of phenylbutazone.

For structural determination, the 2-carboxyethyl derivatives of phenylbutazone were esterified with diazomethane in ether. Chromatography of the esterification product on silica gel resulted in the separation of 2-(methoxycarbonyl) ethyl derivatives $II_Q$ and $II_C$ of phenylbutazone. The structures of $II_Q$ and $II_C$ were determined by NMR analysis.

The NMR spectrum of $II_Q$ in CDCl$_3$ showed signals for butyl at σ0.9, σ1.3–1.6 and σ2.4 (9H), methylene (—CH$_2$<u>CH$_2$</u>CO$_2$CH$_3$) adjacent the ester at σ2.5 (triplet, 2H), ester methyl at σ3.6 (singlet, 3H), O-methylene (—O—<u>CH$_2$</u>CH$_2$—) at σ4.4 (triplet, 2H), and phenyl at σ7.3 (singlet, 10H). The NMR spectrum of $II_C$ showed signals for butyl at σ0.9, σ1.3–1.6 and σ1.9–2.1 (9H), ethylene (—<u>CH$_2$CH$_2$</u>CO$_2$CH$_3$) a σ2.4 (4H), methyl ester at σ3.6 (singlet, 3H), and phenyl at σ7.3 (singlet, 10H).

$II_Q$ and $II_C$ well correspond with a product separately synthesized from phenylbutazone and methyl β-propionate. Accordingly, the 2-carboxyethyl derivatives of phenylbutazone were found to be a mixture of O-(2-carboxy)ethyl ($I_Q$) and C-(2-carboxy)ethyl ($I_C$) derivatives. The mix ratio of $I_Q$ to $I_C$ was about 7:3, and in the present Example, this mixture was directly used.

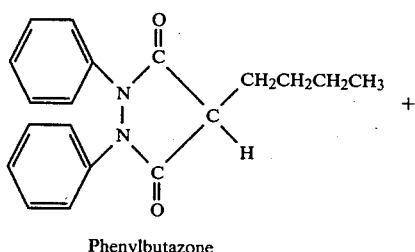

Phenylbutazone

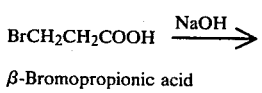

β-Bromopropionic acid

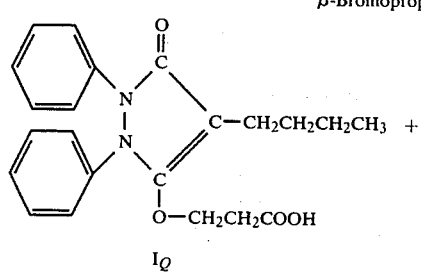

$I_Q$

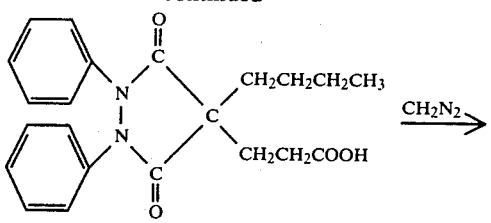

$I_C$

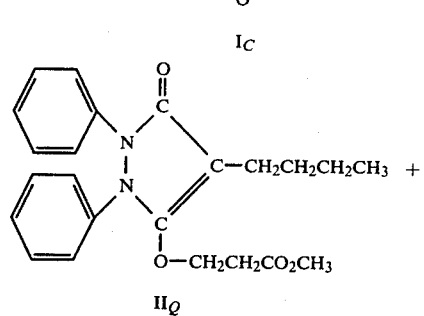

$II_Q$

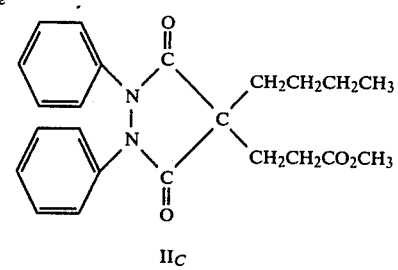

$II_C$

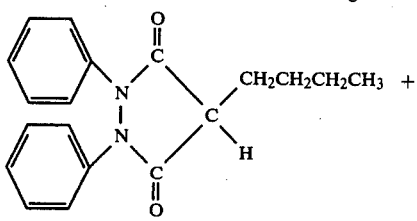

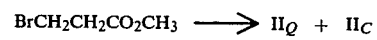

Methyl β-Bromopropionate

A 3 N hydrochloric acid aqueous solution at 30° C. was circulated at a flow rate of 100 ml/min. for 30 minutes through the inside of a nylon-6 tube having an inside diameter of 3 mm and an outside diameter of 5 mm. After the hydrochloric acid had been passed through the tube, deionized water was circulated through the tube to wash the tube. A mixture of 100 ml of a 10% aqueous solution of polyethyleneimine and 500 ml of methanol was circulated at a flow rate of 100 ml/min. for 2 hours at room temperature (about 20° C.–30° C.) through the inside of the nylon tube treated with hydrochloric acid. Then, 200 ml of a 5% by weight methanol solution of dicyclohexylcarbodiimide was added thereto, and subsequently the solution was circulated through the tube at a flow rate of 100 ml/min. for 6 hours. The treating solution was passed out of the tube, and then methanol was circulated through the tube to wash the tube. Then, the tube was dried under reduced pressure.

A solution prepared by dissolving 760 mg of the 2-carboxyethyl derivatives of phenylbutazone and 620 mg of dicyclohexylcarbodiimide in 20 ml of dioxane was circulated at room temperature for 5 hours at a flow rate of 50 ml/min through the inside of the nylon tube treated with polyethyleneimine. The tube was washed with dioxane, and then dried under reduced pressure.

The resulting material having phenylbutazone covalently bonded to the nylon tube treated with polyethyleneimine through a spacer

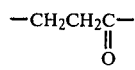

had a thrombus formation time of more than 45 minutes.

A nylon-6 tube whose inside was untreated, and a silicone tube for medical use had a thrombus formation time of 10 minutes and 20 minutes, respectively.

The tube was cut, perpendicularly to the axis, to a thickness of 2 mm to form circular samples. The fibrinolytic activity of the samples was measured. It was found that a fibrin membrane dissolved in a circular shape with a diameter of 8 mm around the samples. The untreated nylon tube and the silicone tube for medical use did not dissolve the fibrin membrane.

EXAMPLE 2

A 4% by weight dioxane solution of the 2-carboxyethyl derivatives of phenylbutazone was circulated at a flow rate of 50 ml/min. at room temperature for 5 hours through the inside of a nylon-6 tube having an inside diameter of 3 mm and an outside diameter of 5 mm. The tube was washed with dioxane and then dried under reduced pressure. The resulting material having the 2-carboxyethyl derivatives of phenylbutazone bonded to the nylon-6 tube by physical adsorption had a thrombus formation time of more than 45 minutes.

EXAMPLE 3

A semisuccinate of 4-butyl-4-hydroxymethyl-1,2-diphenyl-3,5-pyrazolidinedione was synthesized using the method disclosed in U.S. Pat. No. 3,752,894. In the same way as in Example 1, this semisuccinate was bonded to the inner wall of a nylon-6 tube which had been treated with polyethyleneimine. The resulting tube having semisuccinate covalently bonded to the tube through a spacer

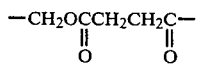

had a thrombus formation time of more than 45 minutes.

EXAMPLE 4

In order to quaternize a nylon tube treated with polyethyleneimine which was obtained as described in Example 1, the inside of the tube was filled with an aqueous solution of ethanol (weight ratio of ethanol to water=1:1) containing 3% by weight of ethyl bromide, and allowed to stand at room temperature for 3 days. The treating solution was passed out of the tube, and the tube was washed with ethanol. Then, in order to change the bromide ion ($Br^-$) to hydroxide ion ($OH^-$), the inside of the tube was filled with a 0.05 N NaOH aqueous solution, and allowed to stand at room temperature for 2 hours. The tube was then washed with water.

The inside of the nylon tube having a quaternary ammonium hydroxide group was filled with an aqueous ethanol solution of oxyphenbutazone (prepared by dissolving 1 g of oxyphenbutazone in a mixed solution of 20 ml of ethanol and 10 ml of water), and then allowed to stand at room temperature for 2 hours. The treating solution was passed out of the tube, and the tube was washed with ethanol and dried.

The resulting material having oxyphenbutazone ionically bonded to the nylon-6 tube had a thrombus formation time of more than 45 minutes.

EXAMPLE 5

As described in Example 4, a nylon-6 tube having a quaternary ammonium hydroxide group was filled with an ethanol solution of mefenamic acid (prepared by dissolving 1 g of mefenamic acid in 30 ml of ethanol) instead of the aqueous ethanol solution of oxyphenbutazone, and was allowed to stand at 60° C. for 2 hours.

The resulting material having mefenamic acid ionically bonded to the nylon-6 tube had a thrombus formation time of more than 45 minutes.

EXAMPLE 6

The inside of a silicone tube having an inside diameter of 3 mm and an outside diameter of 5 mm was filled with a dimethylformamide solution of indomethacin (prepared by dissolving 1 g of indomethacin in 20 ml of dimethylformamide) and allowed to stand at room temperature for 2 hours. The treating solution was removed from the tube, and the tube was washed with dimethylformamide and then with ethanol, and dried.

The resulting material having indomethacin adsorbed physically to the silicone tube had a thrombus formation time of more than 45 minutes.

EXAMPLE 7

A nylon-6 tube having an outside diameter of 5 mm and an inside diameter of 3 mm was cut in a direction perpendicular to the axis of a thickness of 2 mm., the cut pieces were shaken in a 3 N HCl aqueous solution at 30° C. for 30 minutes. After thorough washing with water, the cut pieces were shaken at 30° C. for 2 hours in a mixed solution of a 10% by weight aqueous solution of polyethyleneimie and 5 times its volume of methanol. Then, a methanol solution of dicyclohexylcarbodiimide (prepared by dissolving 5 g of dicyclohexylcarbodiimide in 100 ml of methanol) in an amount two times the volume of the aqueous solution of polyethyleneimine was added, and the cut pieces were shaken in the mixture of 30° C. for 5 hours. The cut pieces were washed with aqueous methanol and then with water, and dried.

Then, the cut pieces were put into an acetone solution containing 5% by weight of a maleic anhydride/methyl vinyl ether copolymer, shaken in this solution at 30° C. for 5 hours, washed with acetone, and dried.

One cut piece was put into a mixed solution of 0.2 ml of a phosphate buffer solution of urokinase (pH 6.85, 600 units/ml) and 0.2 ml of a phosphate buffer solution of flufenamic acid (pH 7.5, 5 mg/ml), allowed to stand at 4° C. for 45 hours, and washed with a phosphate buffer (pH 7.5) and then with physiological saline.

The sample obtained was placed on a fibrin membrane and allowed to stand at 37° C. for 24 hours. It was found that the fibrin membrane was dissolved in a circular shape with a diameter of 20 mm around the sample.

For comparison, the same treatment as above was performed using 0.2 ml of a phosphate buffer (pH 7.5 instead of 0.2 ml of the phosphate buffer solution of flufenamic acid. It was found that the sample dissolved the fibrin membrane in a circular shape with a diameter of 12 mm.

While the invention has been described in detail and with reference to specific embodiments thereof, it will be apparent to one skilled in the art that various changes and modifications can be made therein without depending from the spirit and scope thereof.

What is claimed is:

1. A process for preparing an antithrombogenic polymeric material, which comprises treating a polymeric material selected from the group consisting of polyacrylic acid, polymaleic acid, polyglutamic acid, alginic acid, polyethyleneimine, polymethacryloyl chloride, a polymer of bisphenol A and epichlorohydrin, polyacrolein, polymaleic anhydride, a polyamide, poly(ethylene terephthalate), a polyurethane, a silicone rubber, polyethylene, polypropylene, polyvinyl chloride, polyvinyl alcohol, polyacrylonitrile, cellulose, cellulose acetate, poly(methylmethacrylate), a polyester elastomer, poly(vinylbenzyl trialkyl ammonium ion), poly(vinylbenzyl dialkyl sulfonium ion), poly(vinylbenzyl trialkyl phosphonium ion), poly(dialkyloctamethylene ammonium ion), poly(N,N-dialkyl-3,5-methylenepiperidinium ion), and poly(dialkylaminoethyl methacrylate), with a solution of a synthetic compound which contributes to dissolution of fibrin, said synthetic compound being selected from the group consisting of a 1,2-diphenylpyrazolidine derivative, an anthranilic acid derivative, a salicylic acid derivative, a cinnamic acid derivative, a β-aryl substituted aliphatic acid, and a carboxylic acid containing a heterocyclic ring thereby to cause the synthetic compound to bond covalently or ionically to the polymeric material.

2. A process for preparing an antithrombogenic polymeric material, which comprises treating a polymeric material having a reactive functional group capable of forming a covalent bond, said reactive functional group being selected from the group consisting of a carboxy group, an amino group, a chloroformyl group, a diazonium group, an azido group, an epoxy group, a formyl group, a bromoacetyl group, an isocyanato group, a carboxylic acid anhydride group, and an imidocarbonato group, with a solution of a synthetic compound which contributes to dissolution of fibrin said synthetic compound being selected from the group consisting of a 1,2-diphenylpyrazolidine derivative, an anthranilic acid derivative, a salicylic acid derivative, a cinnamic acid derivative, a β-aryl substituted aliphatic acid, and a carboxylic acid containing a heterocyclic ring thereby to bond the synthetic compound covalently to the polymeric material.

3. The process of claim 2, wherein the polymeric material having a reactive functional group capable of forming a covalent bond is polyacrylic acid, polymaleic acid, polyglutamic acid, alginic acid, polyethyleneimine, polymethacryloyl chloride, a polymer of bisphenol A and epichlorohydrin, polyacrolein, or polymaleic anhydride.

4. A process for preparing an antithrombogenic polymeric material, which comprises introducing a reactive functional group capable of forming a covalent bond into a polymeric material selected from the group consisting of a polyamide, poly(ethylene terephthalate), a polyurethane, a silicone rubber, polyethylene, polypropylene, polyvinyl chloride, polyvinyl alcohol, polyacrylonitrile, cellulose, cellulose acetate, poly(methylmethacrylate), and a polyester elastomer, and then treating the polymeric material with a solution of a synthetic compound which contributes to dissolution of fibrin said synthetic compound being selected from the group consisting of a 1,2-diphenylpyrazolidine derivative, an anthranilic acid derivative, a salicylic acid derivative, a cinnamic acid derivative a β-aryl substituted aliphatic acid, and a carboxylic acid containing a heterocyclic ring thereby to bond the synthetic compound covalently to the polymeric material.

5. The process of claim 4, wherein the reactive functional group capable of forming a covalent bond is a carboxy group, an amino group, a chloroformyl group, a diazonium group, an azido group, an epoxy group, a formyl group, a bromoacetyl group, an isocyanato group, a carboxylic acid anhydride group, or an imidocarbonato group.

6. A process for preparing an antithrombogenic polymeric material, which comprises treating a polymeric material having an anion exchange group selected from the group consisting of a primary amino group, a secondary amino group, a tertiary amino group, a quaternary ammonium group, a tertiary sulfonium group and a quaternary phosphonium group present at the terminals of, and/or on the side chains of, and/or on the main chains of the polymeric material with a solution of a synthetic compound which contributes to dissolution of fibrin and is capable of forming an anion, said synthetic compound being selected from the group consisting of a 1,2-diphenylpyrazolidine derivative, an anthranilic acid derivative, a salicyclic acid derivative, a cinnamic acid derivative, a β-aryl substituted aliphatic acid, and a carboxylic acid containing a heterocyclic ring thereby to bond the synthetic compound ionically to the polymeric material.

7. The process of claim 6, wherein the polymeric material having an anion exchange group is polyethyleneimine, poly(vinylbenzyl trialkyl ammonium ion), poly(vinylbenzyl dialkyl sulfonium ion), poly(vinylbenzyl trialkyl phosphonium ion), poly(dialkyloctamethylene ammonium ion), poly(N,N-dialkyl-3,5-methylenepiperidinium ion), or poly(dialkylaminoethyl methacrylate).

8. A process for preparing an antithrombogenic polymeric material, which comprises introducing a functional group containing an anion exchange group by chemical reaction into a polymeric material selected from the group consisting of a polyamide, poly(ethylene terephthalate), a polyurethane, a silicone rubber, polyethylene, polypropylene, polyvinyl chloride, polyvinyl alcohol, polyacrylonitrile, cellulose, cellulose acetate, poly(methyl methacrylate), and a polyester elastomer, and then treating the polymeric material with a solution of a synthetic compound which contributes to dissolution of fibrin and is capable of forming an anion, said synthetic compound being selected from the group consisting of a 1,2-diphenylpyrazolidine derivative, an anthranilic acid derivative, a salicylic acid derivative, a cinnamic acid derivative, a β-aryl substituted aliphatic acid, and a carboxylic acid containing a heterocyclic ring thereby to bond the synthetic compound ionically to the polymeric material.

9. The process of claim 8, wherein the anion exchange group is a primary amino group, a secondary amino group, a tertiary amino group, a quaternary ammonium group, a tertiary sulfonium group or a quaternary phosphnium group.

10. A process for preparing an antithrombogenic polymeric material, which comprises treating a polymeric material with a solution of a synthetic compound which contributes to dissolution of fibrin, said synthetic compound being selected from the group consisting of a 1,2-diphenylpyrazolidine derivative, an anthranilic acid derivative, a salicylic acid derivative, a cinnamic acid derivative, a β-aryl substituted aliphatic acid, and a carboxylic acid containing a heterocyclic ring, and with a solution of a fibrinolytic enzyme, thereby to cause a covalent bonding or ionic bonding of said synthetic compound and of the enzyme to the polymeric material.

11. The process of claim 10, wherein the enzyme is urokinase.

* * * * *